US009766310B1

(12) United States Patent
Damadian et al.

(10) Patent No.: US 9,766,310 B1
(45) Date of Patent: Sep. 19, 2017

(54) METHOD AND APPARATUS FOR MAGNETIC RESONANCE IMAGING OF THE CRANIO-CERVICAL JUNCTION

(71) Applicant: Fonar Corporation, Melville, NY (US)

(72) Inventors: Raymond V. Damadian, Woodbury, NY (US); Charles A. Green, Holbrook, NY (US)

(73) Assignee: Fonar Corporation, Melville, NY (US)

( * ) Notice: Subject to any disclaimer, the term of this patent is extended or adjusted under 35 U.S.C. 154(b) by 653 days.

(21) Appl. No.: 14/209,279

(22) Filed: Mar. 13, 2014

Related U.S. Application Data (60) Provisional application No. 61/779,165, filed on Mar. 13, 2013, provisional application No. 61/779,388, filed on Mar. 13, 2013.

(51) Int. Cl.
*G01R 33/36* (2006.01)
*G01R 33/30* (2006.01)

(52) U.S. Cl.
CPC ........... *G01R 33/36* (2013.01); *G01R 33/307* (2013.01)

(58) Field of Classification Search
CPC ............................. G01R 33/36; G01R 33/307
See application file for complete search history.

(56) References Cited

U.S. PATENT DOCUMENTS

| 3,810,254 A | 5/1974 | Utsumi et al. |
| 4,407,292 A | 10/1983 | Edrich et al. |
| 4,411,270 A | 10/1983 | Damadian |
| 4,534,076 A | 8/1985 | Barge |
| 4,534,358 A | 8/1985 | Young |
| D283,858 S | 5/1986 | Opsvik et al. |

(Continued)

FOREIGN PATENT DOCUMENTS

| DE | 3140225 A1 | 4/1983 |
| JP | 1242056 | 9/1989 |

(Continued)

OTHER PUBLICATIONS

Alperin et al., "Quantifying the effect of posture on intracranial physiology in humans by MRI flow studies", Journal of Magnetic Resonance Imaging 22:591-59 (2005).

(Continued)

*Primary Examiner* — Rodney Bonnette
(74) *Attorney, Agent, or Firm* — Lerner, David, Littenberg, Krumholz & Mentlik, LLP (57) ABSTRACT

The disclosure of the present invention provides for an imaging apparatus and methods for imaging the cranio-cervical junction of a patient using magnetic resonance. The apparatus is adapted to slide over the patient's head, and includes a saddle element and a solenoid element. The saddle element has a length that extends along a superior-inferior axis of the patient, and a circumference along an axial plane of the patient when the apparatus is slid over the patient's head, so as to define a substantially cylindrical volume. The solenoid element attaches to the saddle element at about a midpoint of the saddle element's length, so as to be positioned along an axial plane of the patient when the apparatus is slid over the patient's head. This configuration allows for the cranio-cervical junction of the patient to be positioned in the cylindrical volume when the apparatus is slid over the patient's head.

19 Claims, 10 Drawing Sheets

(56) References Cited

U.S. PATENT DOCUMENTS

| | | |
|---|---|---|
| 4,608,991 A | 9/1986 | Rollwitz |
| 4,613,820 A | 9/1986 | Edelstein et al. |
| 4,614,378 A | 9/1986 | Picou |
| 4,629,989 A | 12/1986 | Riehl et al. |
| 4,641,119 A | 2/1987 | Moore |
| 4,651,099 A | 3/1987 | Vinegar et al. |
| 4,663,592 A | 5/1987 | Yamaguchi et al. |
| 4,664,275 A | 5/1987 | Kasai et al. |
| 4,668,915 A | 5/1987 | Daubin et al. |
| 4,672,346 A | 6/1987 | Miyamoto et al. |
| 4,675,609 A | 6/1987 | Danby et al. |
| 4,679,022 A | 7/1987 | Miyamoto et al. |
| 4,707,663 A | 11/1987 | Minkoff et al. |
| 4,766,378 A | 8/1988 | Danby et al. |
| 4,767,160 A | 8/1988 | Mengshoel et al. |
| 4,770,182 A | 9/1988 | Damadian et al. |
| 4,777,464 A | 10/1988 | Takabatashi et al. |
| 4,816,765 A | 3/1989 | Boskamp et al. |
| 4,825,162 A | 4/1989 | Roemer et al. |
| 4,829,252 A | 5/1989 | Kaufman |
| 4,866,387 A | 9/1989 | Hyde et al. |
| 4,875,485 A | 10/1989 | Matsutani |
| 4,908,844 A | 3/1990 | Hasegawa et al. |
| 4,918,388 A | 4/1990 | Mehdizadeh et al. |
| 4,920,318 A | 4/1990 | Misic et al. |
| 4,924,198 A | 5/1990 | Laskaris |
| 4,943,774 A | 7/1990 | Breneman et al. |
| 4,968,937 A | 11/1990 | Akgun |
| 4,975,644 A | 12/1990 | Fox |
| 4,985,678 A | 1/1991 | Gangarosa et al. |
| 5,008,624 A | 4/1991 | Yoshida |
| 5,030,915 A | 7/1991 | Boskamp et al. |
| 5,050,605 A | 9/1991 | Eydelman et al. |
| 5,061,897 A | 10/1991 | Danby et al. |
| 5,062,415 A | 11/1991 | Weatherby et al. |
| 5,065,701 A | 11/1991 | Punt |
| 5,065,761 A | 11/1991 | Pell |
| 5,081,665 A | 1/1992 | Kostich |
| 5,124,651 A | 6/1992 | Danby et al. |
| 5,134,374 A | 7/1992 | Breneman et al. |
| 5,153,517 A | 10/1992 | Oppelt et al. |
| 5,153,546 A | 10/1992 | Laskaris |
| 5,155,758 A | 10/1992 | Vogl |
| 5,162,768 A | 11/1992 | McDougall et al. |
| 5,171,296 A | 12/1992 | Herman |
| 5,194,810 A | 3/1993 | Breneman et al. |
| 5,197,474 A | 3/1993 | Englund et al. |
| 5,207,224 A | 5/1993 | Dickinson et al. |
| 5,221,165 A | 6/1993 | Goszczynski |
| 5,221,902 A | 6/1993 | Jones et al. |
| 5,229,723 A | 7/1993 | Sakurai et al. |
| 5,250,901 A | 10/1993 | Kaufman et al. |
| 5,251,961 A | 10/1993 | Pass |
| 5,256,971 A | 10/1993 | Boskamp |
| 5,274,332 A | 12/1993 | Jaskolski et al. |
| 5,291,890 A | 3/1994 | Cline et al. |
| 5,304,932 A | 4/1994 | Carlson |
| 5,305,365 A | 4/1994 | Coe |
| 5,305,749 A | 4/1994 | Li et al. |
| 5,305,750 A * | 4/1994 | Makita ............. G01R 33/56391 128/118.1 |
| 5,315,244 A | 5/1994 | Griebeler |
| 5,315,276 A | 5/1994 | Huson et al. |
| 5,317,297 A | 5/1994 | Kaufman et al. |
| 5,323,113 A | 6/1994 | Cory et al. |
| 5,349,956 A | 9/1994 | Bonutti |
| 5,382,904 A | 1/1995 | Pissanetzky |
| 5,382,905 A | 1/1995 | Miyata et al. |
| 5,386,447 A | 1/1995 | Siczek |
| 5,394,087 A | 2/1995 | Molyneaux |
| 5,412,363 A | 5/1995 | Breneman et al. |
| 5,436,607 A | 7/1995 | Chari et al. |
| 5,471,142 A | 11/1995 | Wang et al. |
| 5,473,251 A | 12/1995 | Mori |
| 5,475,885 A | 12/1995 | Ishikawa et al. |
| 5,477,146 A | 12/1995 | Jones |
| 5,490,513 A | 2/1996 | Damadian et al. |
| 5,515,863 A | 5/1996 | Damadian |
| 5,519,372 A | 5/1996 | Palkovich et al. |
| 5,548,218 A | 8/1996 | Lu |
| 5,553,777 A | 9/1996 | Lampe |
| 5,566,681 A | 10/1996 | Manwaring et al. |
| 5,578,925 A | 11/1996 | Molyneaux et al. |
| 5,592,090 A | 1/1997 | Pissanetzky |
| 5,606,970 A | 3/1997 | Damadian |
| 5,621,323 A | 4/1997 | Larsen |
| 5,623,241 A | 4/1997 | Minkoff |
| 5,640,958 A | 6/1997 | Bonutti |
| 5,652,517 A | 7/1997 | Maki et al. |
| 5,654,603 A | 8/1997 | Sung et al. |
| 5,666,056 A | 9/1997 | Cuppen et al. |
| 5,671,526 A | 9/1997 | Merlano et al. |
| 5,680,861 A | 10/1997 | Rohling |
| 5,682,098 A | 10/1997 | Vij |
| 5,735,278 A | 4/1998 | Hoult et al. |
| 5,743,264 A | 4/1998 | Bonutti |
| 5,754,085 A | 5/1998 | Danby et al. |
| 5,779,637 A | 7/1998 | Palkovich et al. |
| 5,836,878 A | 11/1998 | Mock et al. |
| 5,862,579 A | 1/1999 | Blumberg et al. |
| 5,929,639 A | 7/1999 | Doty |
| 5,951,474 A | 9/1999 | Matsunaga et al. |
| D417,085 S | 11/1999 | Kanwetz, II |
| 5,983,424 A | 11/1999 | Naslund et al. |
| 5,988,173 A | 11/1999 | Scruggs |
| 6,008,649 A | 12/1999 | Boskamp et al. |
| 6,011,396 A | 1/2000 | Eckels et al. |
| 6,014,070 A | 1/2000 | Danby et al. |
| 6,023,165 A | 2/2000 | Damadian et al. |
| 6,029,082 A * | 2/2000 | Srinivasan ......... G01R 33/34046 324/318 |
| 6,075,364 A | 6/2000 | Damadian et al. |
| 6,122,541 A | 9/2000 | Cosman et al. |
| 6,137,291 A | 10/2000 | Szumowski et al. |
| 6,138,302 A | 10/2000 | Sashin et al. |
| 6,141,579 A | 10/2000 | Bonutti |
| 6,144,204 A | 11/2000 | Sementchenko et al. |
| 6,150,819 A | 11/2000 | Laskaris et al. |
| 6,150,820 A | 11/2000 | Damadian et al. |
| 6,201,394 B1 | 3/2001 | Danby et al. |
| 6,208,144 B1 | 3/2001 | McGinley et al. |
| 6,226,856 B1 | 5/2001 | Kazama et al. |
| 6,246,239 B1 | 6/2001 | Krogmann et al. |
| 6,246,900 B1 | 6/2001 | Cosman et al. |
| 6,249,121 B1 | 6/2001 | Boskamp et al. |
| 6,249,695 B1 | 6/2001 | Damadian |
| 6,285,188 B1 | 9/2001 | Sakakura et al. |
| 6,346,814 B1 | 2/2002 | Carrozzi et al. |
| 6,357,066 B1 | 3/2002 | Pierce |
| 6,369,571 B1 | 4/2002 | Damadian et al. |
| 6,377,044 B1 | 4/2002 | Burl et al. |
| 6,385,481 B2 | 5/2002 | Nose et al. |
| 6,411,088 B1 | 6/2002 | Kuth et al. |
| 6,414,490 B1 | 7/2002 | Damadian et al. |
| 6,424,854 B2 | 7/2002 | Hayashi et al. |
| 6,456,075 B1 | 9/2002 | Damadian et al. |
| 6,504,371 B1 | 1/2003 | Damadian et al. |
| 6,549,800 B1 | 4/2003 | Atalar et al. |
| 6,591,128 B1 * | 7/2003 | Wu ................ G01R 33/34084 324/318 |
| 6,608,917 B1 | 8/2003 | Wei et al. |
| 6,639,406 B1 | 10/2003 | Boskamp et al. |
| 6,656,143 B2 * | 12/2003 | Browd ................ A61B 90/14 602/13 |
| 6,677,753 B1 | 1/2004 | Danby et al. |
| 6,792,257 B2 | 9/2004 | Rabe et al. |
| 6,801,038 B2 | 10/2004 | Carrozzi et al. |
| 6,806,711 B2 | 10/2004 | Reykowski |
| 6,850,064 B1 | 2/2005 | Srinivasan |
| 6,850,067 B1 | 2/2005 | Burl et al. |
| 6,882,149 B2 | 4/2005 | Nitz et al. |
| 6,882,877 B2 | 4/2005 | Bonutti |
| 6,894,495 B2 | 5/2005 | Kan |
| 6,954,069 B2 | 10/2005 | Harvey et al. |

(56) References Cited

U.S. PATENT DOCUMENTS

| | | | |
|---|---|---|---|
| 6,975,115 B1 | 12/2005 | Fujita et al. | |
| 6,980,002 B1 | 12/2005 | Petropoulos et al. | |
| 7,046,006 B2 | 5/2006 | Creemers et al. | |
| 7,049,819 B2 | 5/2006 | Chan et al. | |
| 7,123,008 B1 | 10/2006 | Damadian et al. | |
| 7,221,161 B2 | 5/2007 | Fujita et al. | |
| 7,245,127 B2 | 7/2007 | Feng et al. | |
| 7,348,778 B2 | 3/2008 | Chu et al. | |
| 7,450,985 B2* | 11/2008 | Meloy | A61B 5/0555 128/870 |
| 7,474,098 B2 | 1/2009 | King | |
| 7,551,954 B2* | 6/2009 | Green | A61B 5/0555 5/617 |
| 7,680,525 B1 | 3/2010 | Damadian et al. | |
| 7,701,209 B1 | 4/2010 | Green | |
| 7,835,497 B2* | 11/2010 | Haras | A61B 5/1075 378/98 |
| 8,055,326 B1* | 11/2011 | Dworkin | G01R 33/307 600/410 |
| 9,138,164 B2* | 9/2015 | Driemel | A61B 5/0555 |
| 2001/0029330 A1 | 10/2001 | Nose et al. | |
| 2002/0013524 A1 | 1/2002 | Hayashi et al. | |
| 2002/0021128 A1 | 2/2002 | Kuhara | |
| 2002/0032927 A1 | 3/2002 | Dinkler | |
| 2002/0101241 A1 | 8/2002 | Chui | |
| 2002/0123681 A1 | 9/2002 | Zuk et al. | |
| 2002/0196021 A1 | 12/2002 | Wang | |
| 2003/0026469 A1 | 2/2003 | Kreang-Arekul et al. | |
| 2003/0059476 A1 | 3/2003 | Wang | |
| 2003/0210049 A1 | 11/2003 | Boskamp et al. | |
| 2003/0214301 A1 | 11/2003 | Lee | |
| 2005/0020945 A1 | 1/2005 | Tosaya et al. | |
| 2005/0122343 A1 | 6/2005 | Bailey et al. | |
| 2006/0051814 A1 | 3/2006 | Jackowski et al. | |
| 2007/0073195 A1 | 3/2007 | Chen | |
| 2010/0033183 A1* | 2/2010 | Ochi | G01R 33/34046 324/313 |
| 2011/0009749 A1 | 1/2011 | Zamboni | |
| 2011/0026801 A1* | 2/2011 | Dohata | G01R 33/34007 382/131 |

FOREIGN PATENT DOCUMENTS

| | | |
|---|---|---|
| JP | 4-332531 | 11/1992 |
| JP | 62-26052 | 8/1994 |
| JP | 08-050843 A | 2/1996 |
| WO | 97/17896 | 5/1997 |

OTHER PUBLICATIONS

Duan et al. Three-dimensional CT study on normal anatomical features of atlanto-axial joints. 2007 Surg. Radiol. Anat. 29:83-88.

Hill et al. The role of adjustable scout lines in advanced spinal imaging. 2012 Proc. of the N.A.S.S. 27th annual meeting The Spine Journal 12 p.142S paper#P97.

Karhu et al. Kinematic magnetic resonance imaging of the upper cervical spine using a novel positioning device. 1999 SPINE 24:2046-2056.

Koller et al. Assessment of two measurement techniques of cervical spine and C1-C2 rotation in the outcome research of axis fractures 2010 SPINE 35:286-290.

Salem et al. In vivo three-dimensional kinematics of the cervical spine during maximal axial rotation 2013 Manual therapy 18:339-344.

U.S. Appl. No. 14/208,343, filed Mar. 13, 2014.

Weis et al., Simulation of the influence of magnetic field inhomogeneity and distortion correction in MR imaging, vol. 8, No. 4, p. 483-489, 1990 (Abstract).

"The design and construction of high field-uniformity permanent magnet system for MRI" Feng, Z.X.; Jiang, X.H.;Han, S.; Magnetics, IEEE Transactions on vol. 28, Issue 1, Jan. 1992 pp. 641-643.

Guclu et al., A method for Preamplifier-Decoupling Improvement in Quadrature Phased-Array Coils, Journal of Magnetic Resonance Imaging, 19:255-258, 2004.

Feng, et al., A New Phased Array Spine Coil for Vertical Field MRI System, Proc. Intl. Soc. Mag. Reson. Med. 11, 2003.

Three Dimensional Analysis of Spinal Deformities, M. D'Amico, et al., (Eds.), IOS Press, 1995, pp. 445-451.

Jinkins et al., Upright, Weight-bearing, Dynamic-kinetic Magnetic Resonance Imaging of the Spine—Review of the First Clinical Results, 2003, J HK Coll. Radiol., 6:55-74.

Ibell, The Design and Modelling of 2D Phases Arrays for MRI, Oct. 2003, Thesis, The University of Queensland.

Roemer, et al., The NMR Phases Array, Nov. 1990, Magenetic Resonance in Medicine 16, 192-225.

Bottomley et al., What is the Optimum Phased Array Coil Design for Cardiac and Torso Magnetic Resonance?, MRM 37:591-599, 1997.

Damadian et al., "The Possible Role of Cranio-Cervical Trauma and Abnormal CSF Hydrodynamics in the Generis of Multiple Sclerosis", Physiol. Chem. Phys. & Med. NMR (Sep. 20, 2011) 41:1-17.

Zamboni et al (CSF dynamics and brain volume In multiple sclerosis are associated with extracranial venous flow anomalies: a pilot program), Apr. 2010.

Hofmann et al (Phase-Contrast MR Imaging of the Cervical CSF and Spinal Cord: Volumetric Motion Analysis in Patients with Chiari I Malformation. AJNR AM J Neuroradial 21:151-158, Jan. 2000).

Batzdorf et al (Chiari malformation and syringomyelia, 2008).

Zamboni et al (Intracranial venous haemodynamics in multiple sclerosis, 2007).

Kowalski et al. Jul./Aug. 1987, Am. J. NeuroRadiol. 8:697-702.

Netto. Dec. 2006, BSc Thesis Mechanical Engineering, Edith Cowan University, Australia, 145 pages.

* cited by examiner

METHOD AND APPARATUS FOR MAGNETIC RESONANCE IMAGING OF THE CRANIO-CERVICAL JUNCTION

CROSS-REFERENCE TO RELATED APPLICATIONS

The present application claims the benefit of the filing date of U.S. Provisional Patent Application Nos. 61/779,388 and 61/779,165, both filed Mar. 13, 2013, the disclosures of which are hereby incorporated herein by reference in their entirety.

BACKGROUND

The present application relates to magnetic resonance imaging (MRI) apparatuses and systems, and to methods for using such apparatuses and systems.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to precess in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times from the excited state (also referred to as a T1 relaxation time), as well as from in-phase precession (also referred to as a T2 relaxation time) are the dominant factors in determining signal characteristics. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase, amplitude and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Despite the wide adoption of magnetic resonance imaging, X-ray detection continues to be the primary method used to image certain features or regions of a patient's anatomy. One such anatomical feature or region is the patient's cranio-cervical junction, which is the area of the body where the skull meets the spine. Imaging the cranio-cervical junction (hereinafter, cranio-cervical junction) is important for several reasons. Firstly, the C1 (atlas) and C2 (axis) vertebrae of the patient are positioned at the cranio-cervical junction, and damage to these vertebrae can pose serious and potentially fatal health risks for a patient. For instance, rotation of either the C1 or C2 vertebra can impact cerebral spinal fluid flow to and from the brain. If one of the C1 or C2 vertebrae is rotated improperly, it can significantly cut off flow of the cerebral spinal fluid, which can in turn create pressure buildup in the patient's brain.

Despite the importance of imaging the cranio-cervical junction, repeated imaging, such as for the purpose of monitoring the cranio-cervical junction, would require repeated exposure to X-rays. This repeated exposure itself cause damage to living tissue. It is, therefore, recommended that efforts to reduce exposure continue and that repeated X-ray exposure should be minimized. MRI exams, by comparison, can be repeatedly performed without health concerns, and can provide the same or better level of image detail as can X-ray imaging. In that regard, it is desirable to develop a method of imaging the cranio-cervical junction using MRI.

One drawback to imaging the cranio-cervical junction using MRI systems and methods currently known in the art is poor image quality. Acquiring a high quality image using MRI generally requires maintaining a good signal-to-noise ratio (SNR) between the magnetic resonance signals and any accompanying noise. Achieving a good SNR, or at least an improved SNR, often requires the imaging coil of the MRI system to be placed as close as possible to the anatomy of interest. In the case of the cranio-cervical junction, the anatomy of interest is positioned between the patient's skull and spine, making it difficult to image the cranio-cervical junction using a standard head coil or cervical coil. As such, there is a need for a new coil that improves the SNR of cranio-cervical junction images.

Furthermore, imaging a particular anatomical feature or anatomy of interest within the cranio-cervical junction requires the MRI system to be properly aligned with the anatomy of interest. As such, there is also a need for a coil that has a field sensitivity that corresponds with an orientation or alignment of the coil within the MRI system (e.g., a field sensitivity perpendicular to the main magnetic field.

SUMMARY

The present disclosure is directed to an imaging apparatus for imaging the cranio-cervical junction of a patient using magnetic resonance. The apparatus maybe adapted to slide over the patient's head. The apparatus may include a saddle element defining a substantially cylindrical volume, and a solenoid element disposed substantially circumferentially proximate the circumference of the saddle element, for instance, within the circumference of the saddle element. The solenoid element may include two ring coils spaced apart at a fixed distance (e.g., about two inches). In some examples, the solenoid element may be oval shaped.

In some examples, the solenoid element may be disposed at a midpoint of the length of the saddle element such that each ring coil is spaced equidistant from the midpoint. The two ring coils may be spaced apart so as to concentrate the highest signal-to-noise of the solenoid element at the cranio-cervical junction of a patient positioned in the apparatus. The length of the saddle element may also or alternatively be configured so to as to permit the center of the saddle element to align with the cranio-cervical joint on a common axial plane of the patient's head.

In some examples, the solenoid element may exhibit superior-inferior field sensitivity, and the saddle element may exhibit anterior-posterior field sensitivity. The imaging apparatus may be a dual channel quadrature coil.

In further examples, the apparatus may also include a housing containing the saddle element and the solenoid element. The housing may have two outer loops and two middle loops, each loop being spaced apart from one another along the length of the saddle element. The outer loops may contain a substantial portion of the saddle element, and the inner loops may contain the solenoid element. The housing may further include a gap through which the patient's vision is not fully blocked when the apparatus is slid over the patient's head.

The present disclosure is also directed to an MRI system including a magnet, a patient support to support a patient in an upright or seated position, and the above described apparatus. The field sensitivities of the saddle element and the solenoid element may be oriented relative to the magnet in a manner that is suitable for imaging in the MRI system.

The present disclosure is yet further directed to a method of imaging the cranio-cervical junction of a patient using a magnetic resonance imaging system. The method may include: acquiring a first magnetic resonance image of the patient, identifying two or more landmarks in the first magnetic resonance image, selecting an axis on the first magnetic resonance image in line with or parallel to the two or more indentified landmarks, and acquiring a second magnetic resonance image of the patient along the selected axis. Such acquisition may be conducted using the above described apparatus. The second magnetic resonance image may have a different orientation than the first magnetic resonance image. In some cases, one or more alar ligaments may be present in the second magnetic resonance image.

In some examples, the first magnetic resonance image may be taken along a substantially sagittal plane of the patient, and the second magnetic resonance image along a substantially axial plane of the patient, and the two or more landmarks may include the inferior tip of the clivus and the inferior edge of the occipital bone. In yet further examples, the first magnetic resonance image may taken along a substantially sagittal plane of the patient, and the second magnetic resonance image along a substantially coronal plane of the patient, and the two or more landmarks may include the inferior tip of the clivus and the anterior tip of the dens. In some examples, the first magnetic resonance may acquired based on a measurement of a spin-spin relaxation time, and the second magnetic resonance may be acquired based on a measurement of a spin-lattice relaxation time.

DETAILED DESCRIPTION

The present disclosure provides an imaging apparatus that allows for imaging the cranio-cervical junction of a patient using magnetic resonance imaging ("MRI"). The apparatus serves to improve the quality of imaging yielded by MRI. This and other objectives are realized by use of a dual channel quadrature coil adapted to slide over the head of the patient such that the highest signal-to-noise ratio of the coil is concentrated at the cranio-cervical junction of the patient.

The apparatus may also serve to enable imaging of the cranio-cervical junction of the patient in an upright or seated position or posture. In many cases, such positioning of the patient is critical to diagnosis and treatment monitoring. The apparatus may be designed to further permit recumbent imaging when desired.

The apparatus may yet further serve to enable imaging of the cranio-cervical junction of the patient without blocking or impeding at least some of the patient's vision. For example, the apparatus may have a substantially open design that allows the patient to view a television screen while being imaged in the MRI system.

The present disclosure also provides an MRI system that allows for imaging the cranio-cervical junction of a patient using the apparatus described herein. The system may comprise a magnetic resonance imaging magnet and computer or processor based apparatus that controls a patient support associated with the magnet. The processor based apparatus may operate under the control of instructions that cause the support to align the anatomy of interest with the target position by orienting, translating, or otherwise adjusting its position. In addition, the system may include an upright magnetic resonance imaging magnetic apparatus such as those offered for sale by Fonar Corporation. Nonetheless, some aspects of the disclosure may be equally applicable to a more conventional recumbent scanner.

Yet another object of the present disclosure is to provide a method of imaging the cranio-cervical junction of a patient using the apparatus described herein.

Figure 1:
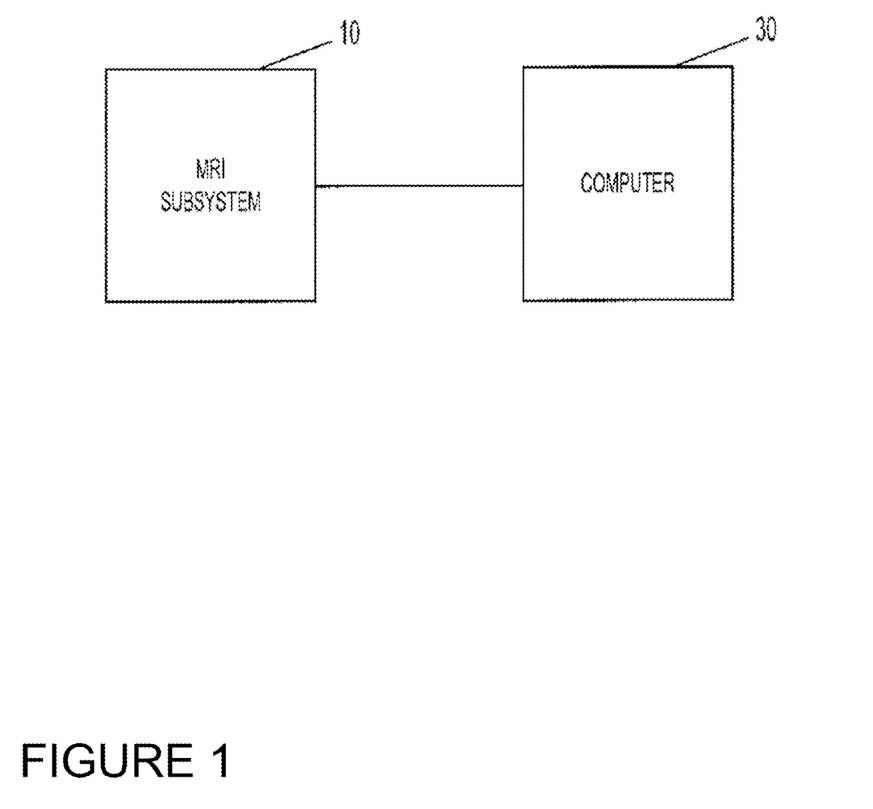
FIG. 1 is a schematic illustration of an MRI system in accordance with an embodiment of the present disclosure.

FIG. 1 illustratively depicts an MRI system in accordance with an aspect of the present disclosure. Turning now to FIG. 1, the system includes an MRI subsystem 10 and a computer 30. The MRI subsystem 10 operates under the control of the computer 30. The subsystem 10 and computer 30 may be connected over a network or via a direct connection. The networks may include a local area network running Ethernet or other network protocols, WiFi or any other type of network that enables communications between two devices. The computer is operable to control the subsystem 10 in acquiring images, including pulse sequence generation, image acquisition and reconstruction.

In general, the subsystem preferably allows a patient to be imaged in positions other than just the recumbent position. For example, FIG. 2 of the current application shows a sectional view of an MRI magnet subsystem 100 for implementing the subsystem 10 shown in FIG. 1, and that can be used in accordance with a preferred embodiment of the present application. MRI magnet subsystem 100 includes a magnet having a ferromagnetic frame 102 for generating a strong, substantially constant static magnetic field, a flux generating means 104 for causing the spin vectors of atomic nuclei within the body to precess at different frequencies, and a patient handling system 106 for supporting the patient and adjusting the patient's position relative to the ferromagnetic frame 102 and flux generating means 104. The ferromagnetic frame 102, flux generating means 104, and patient handling system 106 may be mounted to the MRI magnet subsystem 100. Aside from translation, orientation, etc., of the magnet 102 and flux generation means 104 relative to the patient handling system 106, or vice versa, these components are otherwise fixed in place within the MRI magnet subsystem 100.

The MRI magnet subsystem 100 also includes a radio frequency (RF) imaging apparatus (not shown) for applying RF excitation energy to the body (i.e., using one or more RF transmission coils), and for receiving the MR signals emitted by the body in response to a relaxation from the applied RF energy (i.e., using one or more RF receiving coils). Typically, the RF coils are positioned proximate the anatomy of interest of the patient. In the example of the present disclosure, where it is desired to image the cranio-cervical junction of the patient, the RF coils may be positioned close to the cranio-cervical junction. For instance, transmitter RF coils may be embedded within the patient handling system 106 at a location proximate to the cranio-cervical junction, whereas the receiver RF coils would be worn by the patient. In another example, the transmitter and receiver RF coils may be the same coil (i.e., a transceiver coil) which is worn by the patient. For purposes of illustrative clarity, because the RF imaging apparatus is wearable by the patient, and is not mounted to the other components of the MRI magnet subsystem 100, it is not shown in FIG. 1 and will be described independently and in greater detail below in connection with FIGS. 4 and 5.

Referring first to the components of the MRI magnet subsystem 100 shown in FIG. 1, the ferromagnetic frame 102 includes a first side wall 108 and a second side wall (not shown). The side walls extend vertically. For purposes of clarity, FIG. 2 does not show the second side wall or any of its associated structures, though it should be understood that the second side wall will include elements similar to those contained in first side wall 108. The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole (not shown, but horizontally displaced opposite the first magnetic 132). The first magnetic pole 132 extends from the first side wall 108 towards the second side wall and the second magnetic pole extends from the second side wall towards the first side wall 108. Magnetic poles are generally cylindrical and are coaxial with one another on a common horizontal polar axis. Between the magnetic poles is a gap, also referred to as the patient-receiving space, of the magnet. The gap or patient-receiving space is accessed by the front patient opening 128, the back patient opening 130, the top opening 120 or the bottom opening 126.

Figure 2:
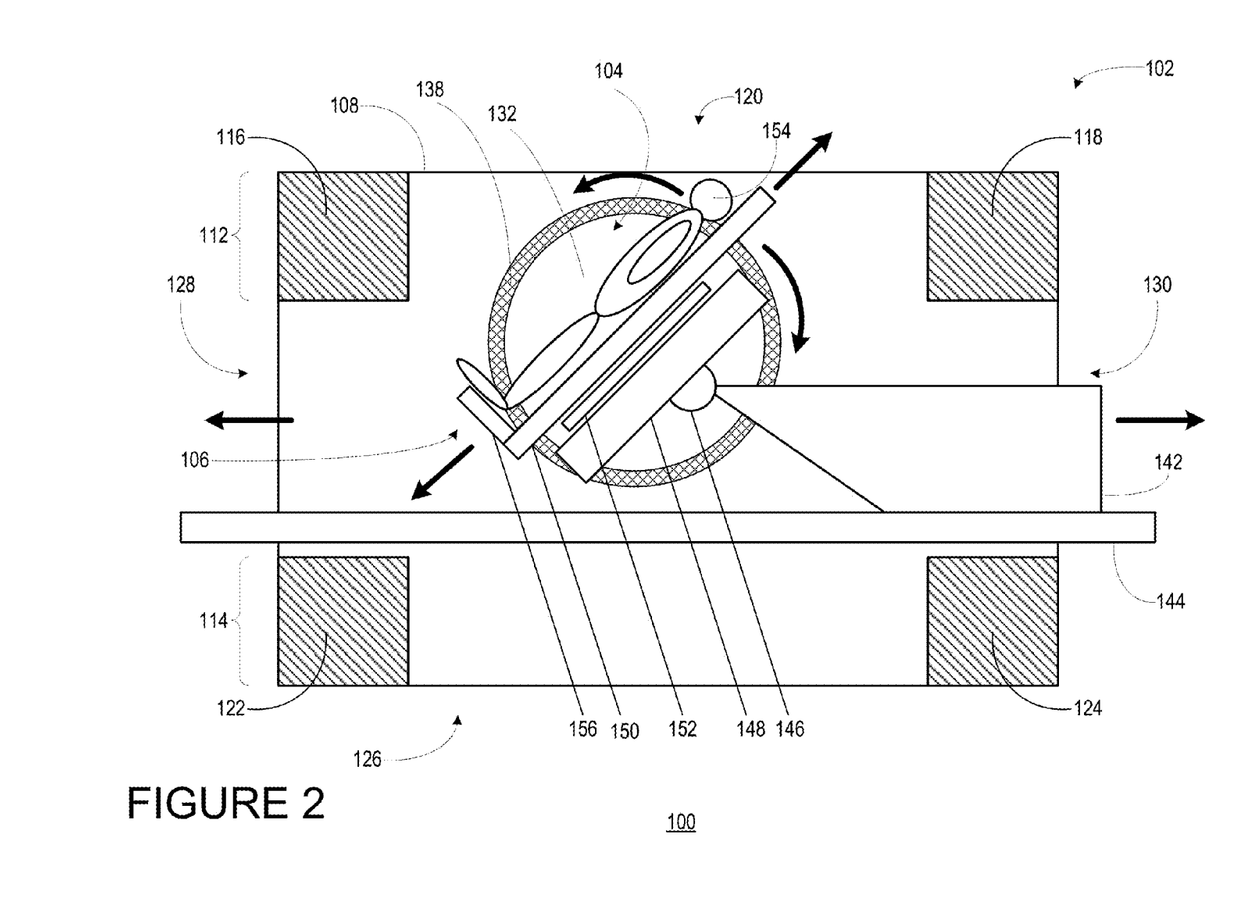
FIG. 2 is a schematic illustration of an example MRI subsystem of the MRI system of FIG. 1.

The flux generating means 104 includes a first electromagnetic coil assembly 138 which surrounds the first magnetic pole 132, and a second electromagnetic coil assembly (not shown, but comparable to the first electromagnetic coil assembly 138) which surrounds the second magnetic pole. These electromagnetic coil assemblies may be either resistive or superconductive.

The patient handling system 106 may be capable of several degrees or axes of motion. The patient handling system 106 may be termed a stand-up patient handling system, although the patient handling system 106 is not limited to standing position applications. The patient handling system 106 may include a carriage 142 mounted on rails 144. The carriage 142 may move linearly back and forth along the rails 144. The rails 144 typically do not block the bottom open space 126. A generally horizontal pivot axis 146 may be mounted on the carriage 142. An elevator frame 148 may be mounted to the pivot axis 146. The carriage 142 may be operable to rotate the elevator frame 148 about the pivot axis 146. A patient support 150 may be mounted on the elevator frame 148. The patient support 150 may be moved linearly along the elevator frame 148 by an actuator 152.

Thus, a patient 154 may be positioned with several degrees of freedom, or along several axes of movement or motion. Specifically, the patient handling system 106 may be capable of moving a patient 154 in any of the two linear directions described above, and may rotate the patient 154 around at least the one rotational axis described above. In the example of FIG. 2, the solid black arrows demonstrate the three axes of movement possible with the patient handling system 106, particularly the linear back-and-forth movement of the carriage along the rails, the rotational movement of the elevator frame 148 about the pivot axis 146, and the linear movement of the patient support 150 along the elevator frame 148. In some examples, such as the example of FIG. 2, the rails 144 may be mounted such that portions of patient 154 may be positioned below the rails 144 through a bottom open space 126.

Often, a foot rest 156 may be used in order to support a patient in a standing position. Given the wide variety of positions possible with the patient handling system 108, many other such supports may be implemented, such as chair seats or straps.

The patient handling system 106 incorporates one or more actuators and an actuation control unit. Actuators may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuation control unit may incorporate a conventional programmable controller, microprocessor, or computer with appropriate input and output interfaces. The actuation control unit is linked to a control computer (such as computer 30) and to manual controls which regulate the patient handling system 106. The actuation control unit may be mounted in proximity to the actuators as, for example, on carriage 142.

Figure 3:
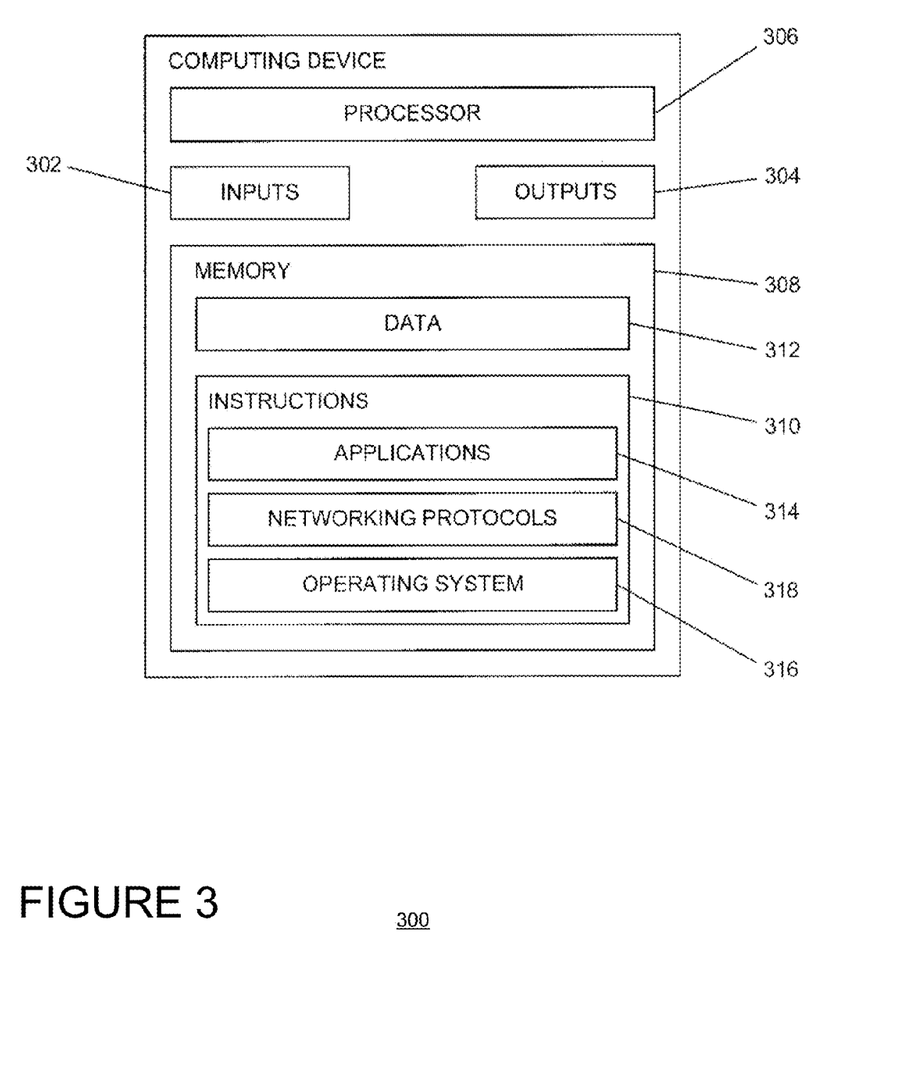
FIG. 3 is a schematic illustration of an example computer of the MRI system of FIG. 1.

FIG. 3 shows an apparatus 300 for implementing the computer 30 depicted in the system presented in FIG. 1. As seen therein, apparatus 300 illustrates one configuration of a computing device that may be used to control the MRI subsystem in accordance with method steps described below.

The apparatus 300 may include, for example, one or more user inputs 302 such as a keyboard and mouse and/or other types of input devices such as pen-inputs, joysticks, buttons, touch screens, etc., as well as a display 304, which could include, for instance, a CRT, LCD, plasma screen monitor, TV, projector, etc. As shown, apparatus 300 further contains a processor 306, and memory or computer readable medium 308.

Memory 308 stores information accessible by the processor 306, including instructions 310 that may be executed by the processor 308 and data 312 that may be retrieved, manipulated or stored by the processor. The memory 308 may be of any type capable of storing information accessible by the processor, such as a hard-drive, ROM, RAM, CD-ROM, DVD, Blu-Ray disk, flash memories, write-capable or read-only memories. The processor 306 may comprise any number of well known processors, such as processors from Intel Corporation and Advanced Micro Devices. Alternatively, the processor 306 may be a dedicated controller for executing operations, such as an ASIC.

The instructions 310 may comprise any set of instructions to be executed directly (such as machine code) or indirectly (such as scripts) by the processor. In that regard, the terms "instructions," "applications," and "programs" are used interchangeably herein. The instructions may be stored in any computer language or format, such as in executable/object code or modules of source code.

Data 312 may be retrieved, stored or modified by processor 306 in accordance with the instructions 310. The data may be stored as a collection of data. For instance, although the invention is not limited by any particular data structure, the data may be stored in computer registers, in a relational database as a table having a plurality of different fields and records, XML documents, or flat files.

The data may also be formatted in any computer readable format such as, but not limited to, binary values, ASCII etc. Similarly, the data may include images stored in a variety of formats. Moreover, the data may include any information sufficient to identify the relevant information, such as descriptive text, proprietary codes, pointers, references to data stored in other memories (including other locations in a network) or information which is used by a function to calculate the relevant data.

Data 312 may include patient identification information. The patient identification information may be useful for properly identifying an image that is displayed on the display 304 as an image of a particular patient, and may further be useful for verifying that the correct image is displayed.

Data 312 may also include information pertaining to the current position and orientation of the patient handling system 106 within the MRI magnet subsystem 100. As described above, the patient handling system 106 is capable of moving along three degrees of freedom, specifically along two linear axes and a third rotational axis. In some examples, the current position and orientation of the patient handling system 106 may be represented in the data 312 in terms of these three axes. In other examples, the current position and orientation of the patient handling system 106 may be represented in the data 312 in terms of a different set of axes, such as in terms of an anterior, a superior, and a left axis of the patient, or in terms of an x, y, and z axis of the MRI magnet subsystem 100. It will be understood by those of ordinary skill in the art that the position and orientation of an object in three-dimensional space may be represented in terms of several sets of axes, and that any of such sets of axes may be used to represent such information in the data 312.

In further examples, the position of the carriage 142 may be represented in terms of its relative position on the rails 144 and the position of the patient support 150 on the elevator frame 148. Such information may be beneficial for determining how much further the carriage 142 and/or patient support 150 may be moved within the patient handling system 106.

Data 312 may further include information pertaining to a user input. For example, the data may include information regarding a current position of a user-controlled cursor appearing on the display 304. The position of such a user-controlled cursor may be represented in the data 312 in terms of an x-coordinate and a y-coordinate corresponding to coordinates of the display screen. The position may further be represented in the data 312 in terms of a three dimensional space, such as the axes described above, such that each point of the display is associated with a coordinate of the MRI magnet subsystem 100. In some aspects of the disclosure, such data may also be displayed to a user, for instance via the display 304.

Although the processor 306 and memory 308 are functionally illustrated in FIG. 3 as being within the same block, it will be understood that the processor and memory may actually comprise multiple processors and memories that may or may not be stored within the same physical housing or location. For example, some or all of the instructions and data may be stored on a computer-readable removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 308 such as hard drives, data centers, server farms or the like.

In addition, the memory 308 in apparatus 300 may include one or more applications or programs 314 adapted to provide any of the functions described with respect to the computer 30 and in accordance with the various aspects of the invention discussed above and below. Each device may include and execute specific instructions or applications, desirably under management of the processor 306 in conjunction with an operating system 316 and networking protocols instructions 318 to provide the functionality described above.

Figure 4:
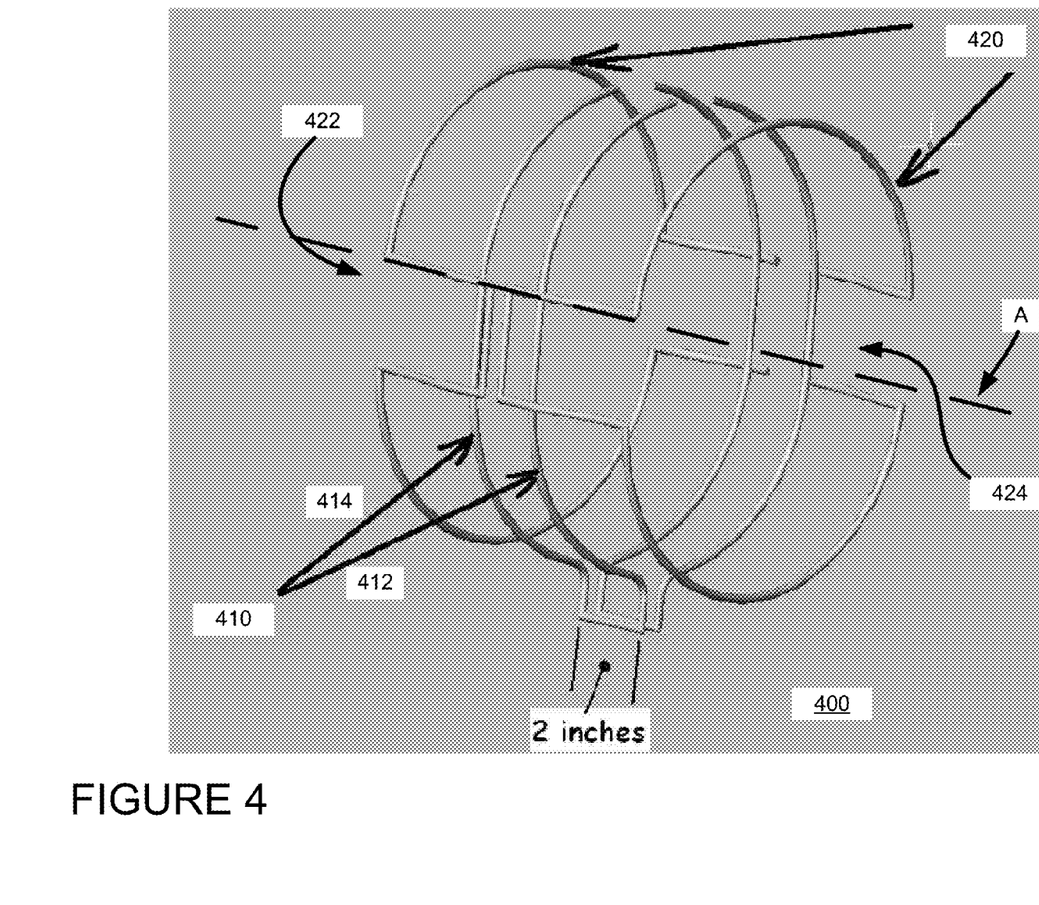
FIG. 4 is a perspective view of an example imaging apparatus of the MRI system of FIG. 1.

Referring now to the RF imaging apparatus of the MRI subsystem 100 of FIG. 2, FIG. 4 illustrates an apparatus 400 designed specially for imaging the cranio-cervical junction of the patient. The apparatus 400 has been found to produce higher quality images of the cranio-cervical junction, as compared to other imaging coils, coil combinations, and apparatuses known in the art (e.g., a standard quadrature head coil, a standard cervical coil, any other coil developed to date that will image in the UPRIGHT® Multi-Position™ MRI produced by Fonar Corporation) due to an improved signal-to-noise ratio (SNR). The apparatus is specially adapted to slide far enough over the patient's head (i.e., before the patient's shoulders prevent the coils of the apparatus from going any lower) such that the highest SNR is concentrated at a relatively narrow band reaching the cranio-cervical joint without the shoulders of the patient interfering with proper positioning of the apparatus 400.

The apparatus 400 includes a unique coil geometry combination of an oval solenoid coil element 410 nested and centered within a saddle coil element 420, such that the circumference of the solenoid coil element 410 aligns with that of the saddle coil element 420 proximate to one another. The frame of the saddle coil element 420 is substantially cylindrical in shape and defines a substantially cylindrical volume therein. The frame is shaped so as to permit a patient's head to fit through the cylindrical volume, and as such is itself oval-shaped to better conform to the geometry of the patient's head.

The solenoid coil element 410 includes two coil rings 412 and 414. In the example of FIG. 4, the rings are positioned at about a midpoint of the length of the saddle coil element 420, although positioning of the rings may be different in other examples to accommodate the specific dimensions of the patient's body (e.g., so as to properly align the rings with the cranio-cervical junction). As stated above, the rings are oval or oblong shaped in the example of FIG. 4, although the rings in other examples of the disclosure may be rounder. Also, as stated above, the rings shown in FIG. 4 are nested within the saddle coil element, meaning that the circumference of each ring is slightly smaller than the circumference of the saddle coil element 420 at the midpoint of the saddle coil element's length. In other examples of the disclosure, however, the rings may be disposed slightly outside of the saddle coil element 420, such that the rings have a larger circumference, so long as the rings are still strong enough to provide good image quality of the cranio-cervical junction. Also, in the example of FIG. 4, the solenoid coil element 410 is attached to the saddle coil element 420 such that both elements may be slid over the patient's head in a single motion and at the same time. However, in other examples of the disclosure, the coils do not need to be attached, so long as they fit together over the anatomy of interest.

The rings have a predetermined spacing or fixed distance designed to concentrate the highest SNR at the cranio-cervical junction of the patient. For instance, in the example of FIG. 4, the rings are spaced about two inches apart (e.g., more than 1.5 inches apart and less than 2.5 inches apart). In other examples, the rings may be spaced more than an inch and a half apart.

When worn on a patient, the apparatus 400 is oriented such that a line through the center of the cylindrical volume of the saddle coil element 420 extends along a superior-inferior axis A of the patient's body and the circumference of the cylindrical volume extends axially outward from the superior-inferior axis A (i.e., on an axial plane of the patient's body). In this manner, when the patient puts the apparatus on, the patient's head slides into the apparatus 400 at a first end opening 422 and may (for some patients) protrude through the apparatus out of the opposing second end opening 424. When the apparatus 400 is at rest over the patient's head, the center of each of the saddle coil element 420 and the solenoid coil element 410 may be aligned axially with the cranio-cervical joint of the patient (i.e., along an axial plane of the patient).

In order to achieve the improved SNR at the cranio-cervical junction, the solenoid element 410 is positioned around the neck of the patient such that it exhibits a field sensitivity along a superior-inferior axis of the patient. Additionally, since the cranio-cervical junction is located closer to the back of the patient's body, as opposed to the side, the saddle coil element 420 is positioned in front of and behind the patient so as to exhibit a field sensitivity along an anterior-posterior axis of the patient. In this manner, the apparatus is specially configured to operate in an MRI magnet subsystem having a transaxial magnetic field orientation, such as the UPRIGHT® Multi-Position™ MRI or the MRI magnet subsystem 100 of FIG. 2. It will be appreciated that this design will not work in a solenoid field magnet, since the coil elements must be positioned perpendicular to the main magnetic field. As for imaging the patient in a vertical field magnet, the above apparatus may possibly be reoriented relative to the magnet by having the patient lie on his or her side. Alternatively, the apparatus may be specially designed so as to align the field sensitivity of the saddle coil along the patient's left-right axis (i.e., the width of the oval shape). As a further alternative, if the apparatus is designed with a circular shape, the apparatus may be fit over the patient's head in a rotated alignment (e.g., a quarter turn from the normal alignment) so as to align the field sensitivity of the saddle coil is along the patient's left-right axis perpendicular to the axis of vertical field magnet's main magnetic field. Any of the above alternatives achieve at least some of the advantages of the present disclosure.

Due to the perpendicular field sensitivity of the solenoid coil element 410 relative to the saddle coil element 420, the apparatus 400 may be a dual channel quadrature coil. Accordingly, the magnetic resonance signals received at each of the coil elements may be analyzed or processed together, and a single MRI image may be generated through a combination or composite of the received signals.

Figure 5:
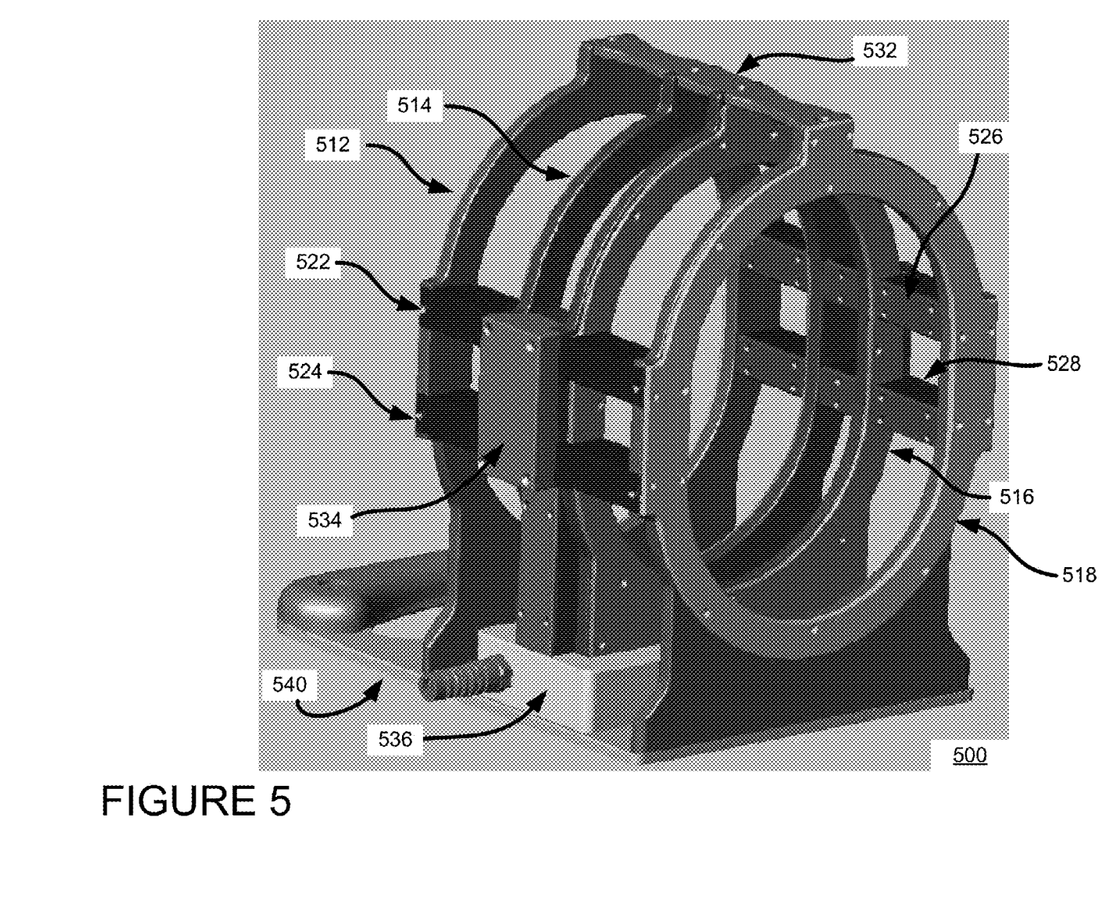
FIG. 5 is a perspective view of a cage housing the imaging apparatus of FIG. 4.

The apparatus 400 of FIG. 4 may be contained in a housing or cage. FIG. 5 illustrates a perspective view of one such cage 500. The cage 500 includes four loops 512, 514, 516 and 518 each situated on a different axial plane, such that the loops are distanced from one another axially (i.e., along the length axis of the saddle coil) at a fixed distance. The two outer loops 512 and 518 contain a substantial portion of the saddle coil element 420 of FIG. 4, and the two inner loops 514 and 516 contain the solenoid coil element 410. The remaining portions of the saddle coil element 420 are contained within lateral bars 522, 524, 526, and 528. A front bar 532 provides further structural reinforcement to the cage 500. A side panel 534 houses a tuning network for the saddle coil element 420, and a back panel 536 houses a tuning network for the solenoid coil element 410.

The cage 500 may be removeably or permanently mountable or attachable to a support. In the example of FIG. 5, the cage 500 is designed with a substantially flat back wall 540 so as to permit mounting from behind to a support, such as the patient support 106 of FIG. 2. In this manner, the patient's head may be comfortably slid into the cage 500 without placing undue weight or pressure against the patient's neck or shoulders.

One benefit of the cage 500 of FIG. 5 is its relatively open nature. Even while the patient is wearing the cage 500, there are several gaps through which the patient's view is not blocked or fully impeded. As such, the patient may be free to watch a television screen during an MRI imaging procedure.

Due to the improved SNR of the above described imaging apparatus, an MRI system including the imaging apparatus may be used to diagnose anatomical features of the patient's cranio-cervical junction (such as the C1 and C2 vertebrae and alar ligaments), as well as to monitor treatment of the aforementioned anatomical features.

Figure 6:
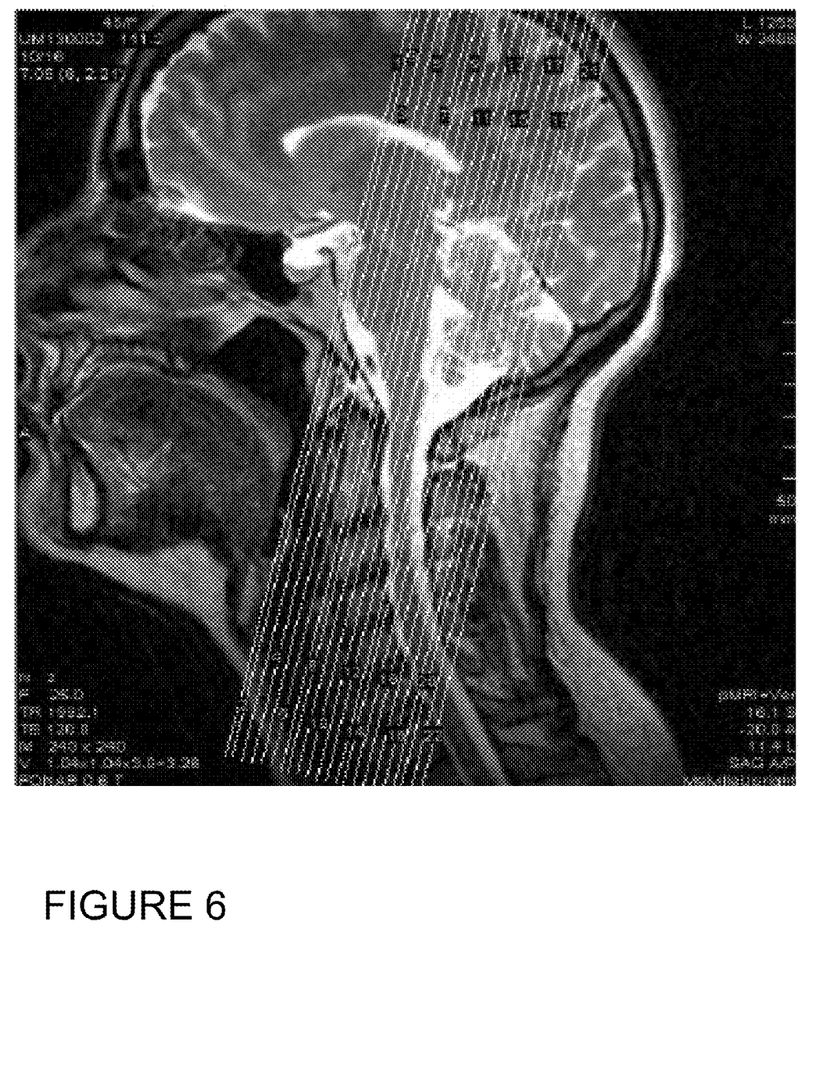
FIG. 6 is a sagittal scout MRI image in accordance with an embodiment of the present disclosure.

FIG. 6 illustrates an example scout MRI image showing a sagittal plane focused at or around the cranio-cervical junction of a patient. The image of FIG. 6 is taken using a T2 scan (which measures T2 relaxation time), although one skilled in the art would recognize that other scans may alternatively be performed. The example image of FIG. 6 also shows several lines, twenty-two (22) in total, extending from the anterior spine through the foramen magnum. Each line corresponds to a substantially coronal plane of the patient (hereinafter, referred to plainly as coronal planes) and represents a candidate coronal MRI image that may be acquired by the MRI system.

Figure 7:
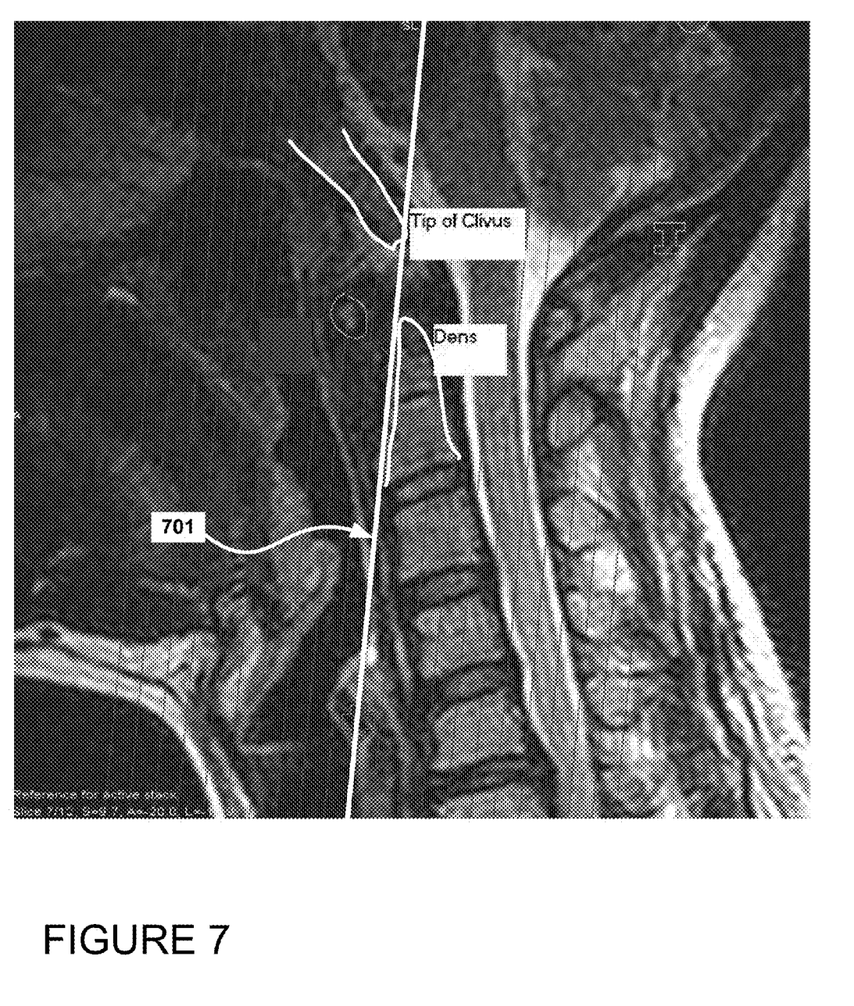
FIG. 7 is an enlarged view of a portion of the MRI image of FIG. 6.
Figure 8:
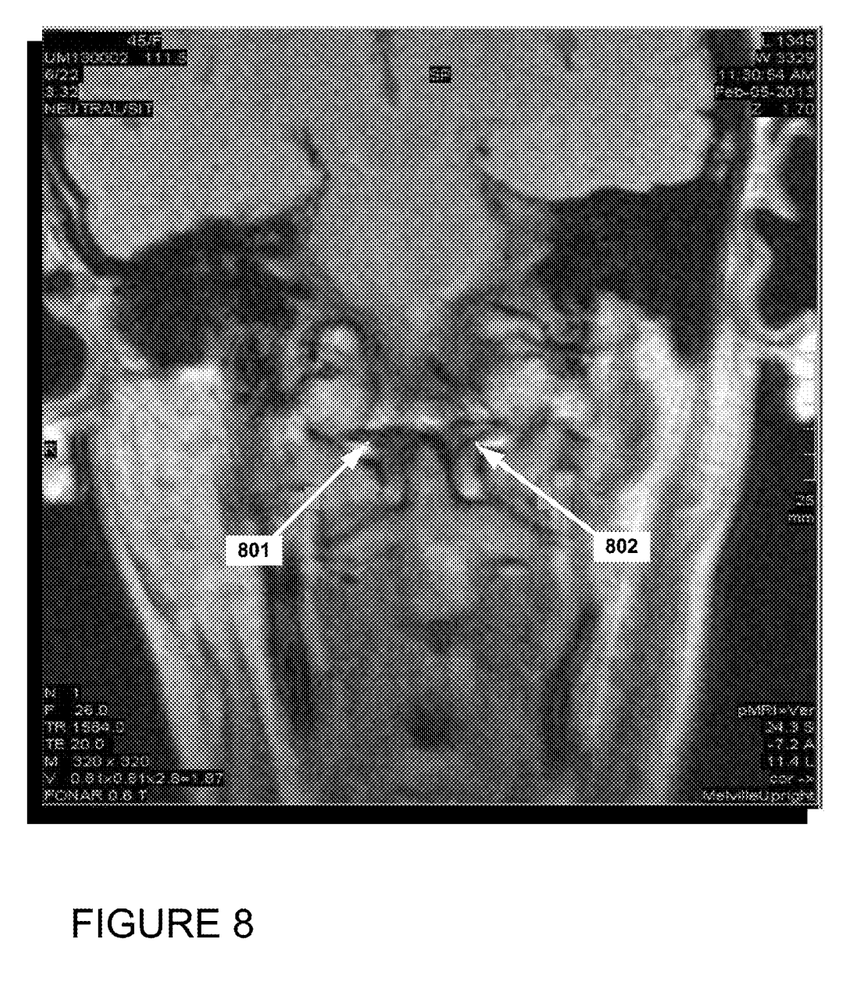
FIG. 8 is a coronal MRI image in accordance with an embodiment of the present disclosure.

In order to select the appropriate coronal MRI image to be acquired for purposes of diagnosing and monitoring features of the cranio-cervical junction, certain landmark features may be selected from the scout sagittal image of FIG. 6. For instance, FIG. 7 shows an enlarged view of a portion of the scout sagittal image of FIG. 6. In the portion of FIG. 7, the inferior tip of the clivus and the anterior tip of the dens are both outlined. These tips may be used to select an appropriate coronal slice from a stack of candidate coronal MRI image slices. In the example of FIG. 7, line 701 is the slice closest to both tips and is therefore selected. The selected coronal slice represented by line 701 is shown in FIG. 8. As seen in FIG. 8, the alar ligaments of the cranio-cervical junction (labeled 801 and 802) are present in the selected coronal slice. Thus, the image shown in FIG. 8 is especially beneficial for diagnosing and monitoring tears in the alar ligaments.

Figure 9:
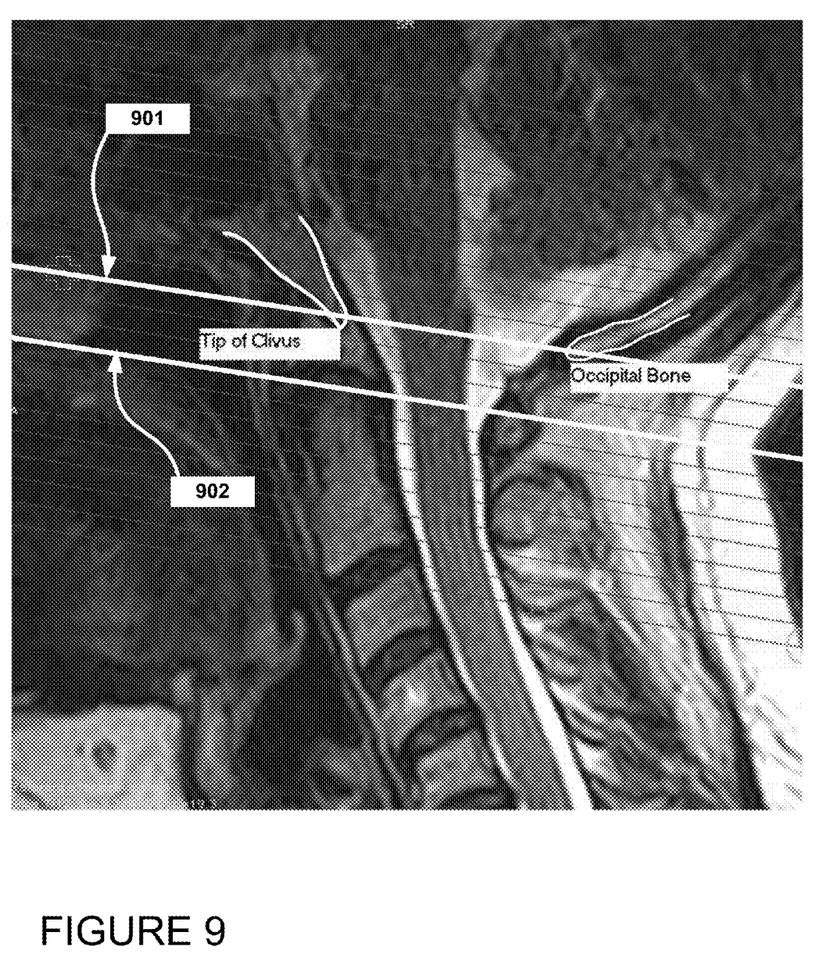
FIG. 9 is an enlarged view of another portion of the MRI image of FIG. 6.

To further illustrate, FIG. 9 shows an enlarged view of a different portion of the scout sagittal image of FIG. 6. In the portion of FIG. 9, the inferior tip of the clivus and the inferior edge of the occipital bone are both outlined. These features may be used to line up an appropriate axial slice from a stack of candidate axial MRI image slices. In the example of FIG. 9, a line 901 connecting the inferior tip of the clivus and the inferior edge of the occipital bone is parallel to the desired axial slice (line 902) having the C1 vertebra. Thus, by lining up line 901, the stack of candidate axial MRI image slices will include the desired axial slice represented by line 902, which is then selected to be imaged. In some examples, the axial slice image is acquired using a T1 scan (measuring T1 relaxation time), although one of skill in the art would recognize that other scans may alternatively be performed.

An axial MRI image acquired along line 902, parallel to line 901, includes the C1 vertebra. Thus, acquiring an axial MRI image along the selected line 902 is especially beneficial for diagnosing and monitoring defects in the C1 vertebra, such as a rotation of the C1 vertebra due to malalignment (which may impact cerebral spinal fluid flow to and from the brain). Such rotation may be measured and/or evaluated from the axial MRI image using the methods and procedures described in commonly owned U.S. Provisional Patent Application No. 61/779,165 and concurrently filed U.S. Patent application entitled "Cervical Vertebra Angle Measurement" the disclosures of which are hereby incorporated by reference herein in their entirety.

Although FIGS. 7 and 9 depict portions of the same scout sagittal scan, the candidate MRI scan stacks in each figure are oriented differently. Changing the orientation of the candidate MRI slice stack may be controlled by instructions provided from the computing apparatus 300 of the MRI system.

Operations in accordance with aspects of the disclosure will now be described with reference to the figures. It should be understood that the following operations do not have to be performed in the precise order described below. Rather, various operations can be handled in a different order or simultaneously. It should also be understood that these operations do not have to be performed all at once. For instance, some operations may be performed separately from other operations.

Figure 10:
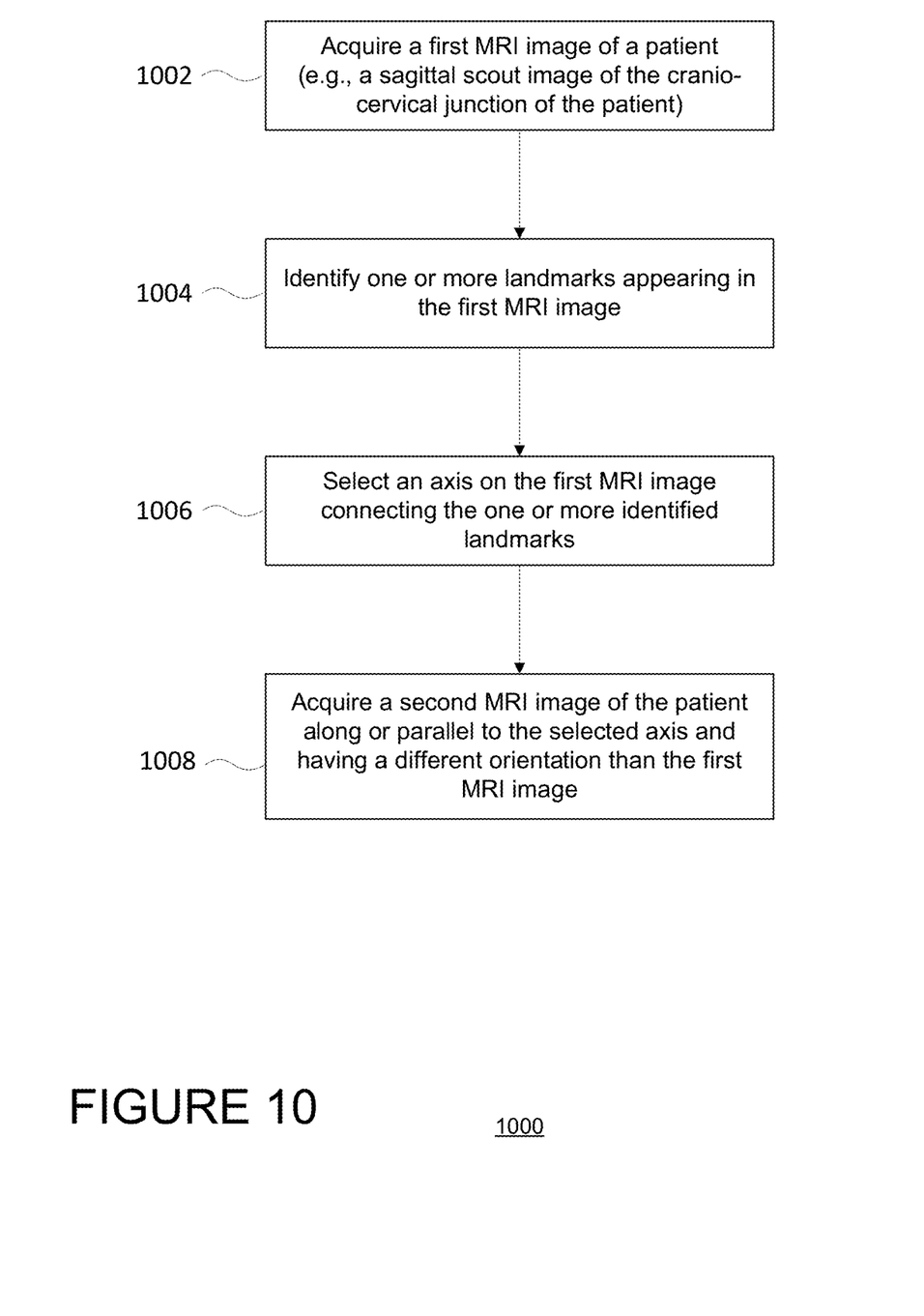
FIG. 10 is a flow chart illustrating a method of operation of the MRI system of FIG. 1 in accordance with an embodiment of the present disclosure.

FIG. 10 is a flow chart 1000 illustrating a method of using the coil apparatus of the present disclosure to image features of the cranio-cervical junction. In block 1002, a first MRI image of the patient is acquired. The first MRI image may be a sagittal scout image of the cranio-cervical junction of the patient, such as the image shown in FIG. 6 (or the zoomed-in portions shown in FIGS. 7 and 9).

In block 1004, two or more landmarks appearing in the first magnetic resonance image are identified. In one example, for instance when setting up a coronal MRI scan (as shown in FIG. 7) the landmarks may include the anterior tip of the dens and the inferior tip of the clivus. In another example, for instance when setting up an axial MRI scan (as shown in FIG. 9), the landmarks may include the inferior edge of the occipital bone and the inferior tip of the clivus. Of course, other landmarks (which may include positions relative to identified landmarks, e.g., "immediately below the inferior tip of the clivus" or "slightly below the inferior edge of the occipital bone") may be used to set up other useful MRI scans known in the art.

In block 1006, an axis or line connecting the two or more identified landmarks is selected such that the identified landmarks appear on the connecting line. A single MRI image may then be taken on a desired plane along the connecting line (as in the example of FIG. 7), or parallel to the connecting line (as in the example of FIG. 9). As explained above, selecting the connecting line may in some cases involve aligning the anatomical landmarks with a new slice stack of scout lines. In some instances, the landmarks may already be properly aligned with one of the scout lines, in which case block 1006 only requires that the alignment be maintained for the desired line or axis to be selected.

Lastly, in block 1008, a second MRI image of the patient is acquired using the above described imaging apparatus. The second magnetic image may be axial, coronal, substantially axial, or substantially coronal. The second MRI image may have a different orientation than the first MRI image, while maintaining the presence of the two or more landmarks on the second MRI image (as in the example of FIG. 7) or maintaining the parallelism between the second MRI image plane and the line connecting the two or more landmarks (as in the example of FIG. 9). As described above, the second MRI image may be used to diagnose such conditions as torn alar ligaments (in the case of the coronal scan represented by line 701 of FIG. 7) or a rotated C1 vertebra (in the case of the axial scan represented by line 901 of FIG. 9). Other conditions known in the art and related to the cranio-cervical junction may also be diagnosed and/or monitored.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An imaging apparatus for imaging the cranio-cervical junction of a patient using magnetic resonance, the apparatus being adapted to slide over the patient's head and comprising:
   a saddle element defining a cylindrical volume; and
   a solenoid element disposed within the circumference of the saddle element, wherein the length of the saddle element is configured so as to permit the center of the saddle element to align with the cranio-cervical joint on an axial plane of the patient.

2. The apparatus of claim 1, wherein the solenoid element includes two ring coils spaced apart at a fixed distance and is disposed at a midpoint of the length of the saddle element such that each of the two ring coils is spaced equidistant from the midpoint.

3. The imaging apparatus of claim 1, wherein the solenoid element includes two ring coils spaced apart at a fixed distance, and wherein the two ring coils are spaced apart so as to concentrate the highest signal-to-noise of the solenoid element at the cranio-cervical junction of a patient positioned in the apparatus.

4. The imaging apparatus of claim 1, wherein the solenoid element includes two ring coils spaced apart at a fixed distance of two inches.

5. The imaging apparatus of claim 1, wherein the solenoid element exhibits superior-inferior field sensitivity, and wherein the saddle element exhibits anterior-posterior field sensitivity.

6. The imaging apparatus of claim 1, wherein the imaging apparatus is a dual channel quadrature coil.

7. The imaging apparatus of claim 1, wherein the solenoid element is oval.

8. The imaging apparatus of claim 1, further comprising a housing containing the saddle element and the solenoid element, the housing including two outer loops and two middle loops, each loop spaced apart from one another along the length of the saddle element, the outer loops containing a majority of the saddle element and the inner loops containing the solenoid element.

9. The imaging apparatus of claim 8, wherein the housing further comprises a gap through which the patient's vision is not fully blocked when the apparatus is slid over the patient's head.

10. An MRI system, comprising:
   a magnet;
   a patient support configured to support a patient in an upright position; and
   the imaging apparatus of claim 1, wherein the field sensitivities of the saddle element and the solenoid element of the apparatus are oriented relative to the magnet in a manner that is suitable for imaging in the MRI system.

11. A method of imaging the cranio-cervical junction of a patient using a magnetic resonance imaging system, comprising:
   acquiring a first magnetic resonance image of the patient;
   identifying two or more landmarks in the first magnetic resonance image;
   selecting an axis on the first magnetic resonance image in line with the two or more indentified landmarks; and
   acquiring a second magnetic resonance image of the patient along or parallel to the selected axis using the imaging apparatus of claim 1, the second magnetic resonance image having a different orientation than the first magnetic resonance image.

12. The method of claim 11, wherein the first magnetic resonance image is taken along a sagittal plane of the patient, and the second magnetic resonance image is taken along a axial plane of the patient.

13. The method of claim 12, wherein the two or more landmarks comprises the inferior tip of the clivus and the inferior edge of the occipital bone.

14. The method of claim 11, wherein the first magnetic resonance image is taken along a sagittal plane of the patient, and the second magnetic resonance image is taken along a coronal plane of the patient.

15. The method of claim 14, wherein the two or more landmarks comprises the inferior tip of the clivus and the anterior tip of the dens.

16. The method of claim 11, wherein the first magnetic resonance image is acquired based on a measurement of a spin-spin relaxation time, and wherein the second magnetic resonance image is acquired based on a measurement of a spin-lattice relaxation time.

17. The method of claim 11, wherein one or more alar ligaments are present in the second magnetic resonance image.

18. An imaging apparatus for imaging the cranio-cervical junction of a patient using magnetic resonance, the apparatus being adapted to slide over the patient's head and comprising:
   a saddle element defining a cylindrical volume; and
   a solenoid element disposed within the circumference of the saddle element, the solenoid element having two ring coils spaced apart so as to concentrate the highest signal-to-noise of the solenoid element at the cranio-cervical junction of a patient positioned in the apparatus.

19. An imaging apparatus for imaging the cranio-cervical junction of a patient using magnetic resonance, the apparatus being adapted to slide over the patient's head and comprising:
   a saddle element defining a cylindrical volume; and
   a solenoid element disposed within the circumference of the saddle element,
   wherein the solenoid element includes two ring coils spaced apart at a fixed distance of two inches.

* * * * *